US006858041B2

(12) United States Patent
Richter et al.

(10) Patent No.: US 6,858,041 B2
(45) Date of Patent: Feb. 22, 2005

(54) IMPLANT INCLUDING A BODY OF NON-RESORBABLE BIOACTIVE MATERIAL

(75) Inventors: Paul Wilhelm Richter, Pretoria (ZA); Michael Edward Thomas, Pretoria (ZA)

(73) Assignee: Technology Finance Corporation (Proprietary) Limited, Sandton (ZA)

( * ) Notice: Subject to any disclaimer, the term of this patent is extended or adjusted under 35 U.S.C. 154(b) by 64 days.

(21) Appl. No.: 10/009,214

(22) PCT Filed: Mar. 7, 2001

(86) PCT No.: PCT/IB01/00313

§ 371 (c)(1),
(2), (4) Date: Nov. 8, 2001

(87) PCT Pub. No.: WO01/66163

PCT Pub. Date: Sep. 13, 2001

(65) Prior Publication Data

US 2003/0100946 A1 May 29, 2003

(30) Foreign Application Priority Data

Mar. 10, 2000 (ZA) .......................................... 2000/1247

(51) Int. Cl.[7] .................................................. A61F 2/28
(52) U.S. Cl. .................................................... 623/11.11
(58) Field of Search ........................... 623/11.11, 16.11, 623/23.5, 23.51, 23.56, 23.61, 23.72–23.76

(56) References Cited

U.S. PATENT DOCUMENTS

| 4,798,585 | A |   | 1/1989  | Inoue et al. |
| 4,839,215 | A | * | 6/1989  | Starling et al. ............. 428/131 |
| 4,863,475 | A | * | 9/1989  | Andersen et al. ........... 128/898 |
| 5,171,326 | A | * | 12/1992 | Ducheyne et al. ......... 623/66.1 |
| 5,192,325 | A | * | 3/1993  | Kijima et al. ............... 424/423 |
| 5,624,463 | A | * | 4/1997  | Stone et al. ............. 623/23.61 |
| 5,769,897 | A | * | 6/1998  | Harle ......................... 424/423 |
| 5,868,796 | A | * | 2/1999  | Buechel et al. .......... 623/16.11 |

* cited by examiner

Primary Examiner—Kevin Shaver
Assistant Examiner—Michael B. Priddy
(74) Attorney, Agent, or Firm—Frommer Lawrence & Haug LLP; William S. Frommer; Matthew K. Ryan

(57) ABSTRACT

An implant includes a body of non-resorbable bioactive material, with zones of resorbable bioactive material located in the body of non-resorbable material. The sizes of a major proportion of the zones of resorbable material are from 10 to 500 microns.

25 Claims, 1 Drawing Sheet

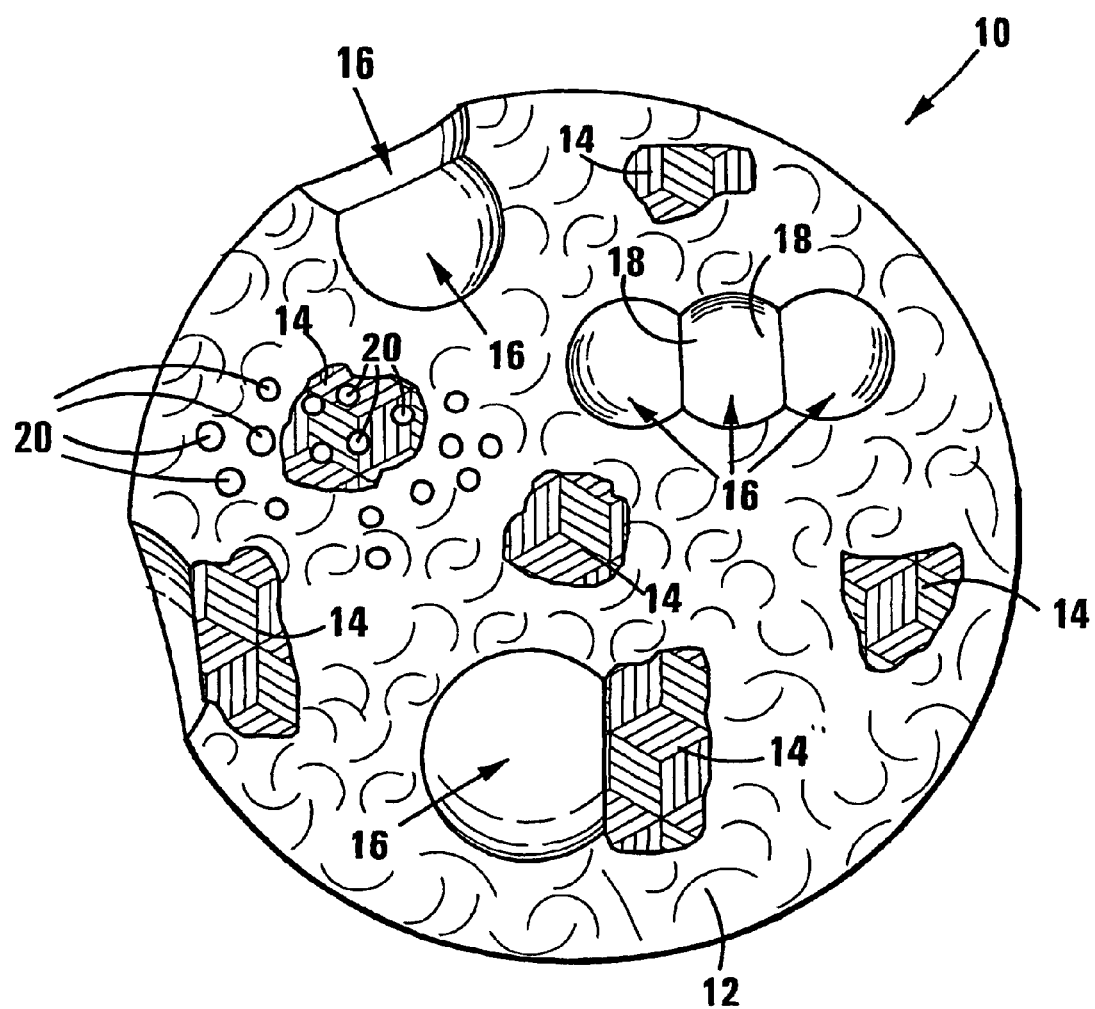

IMPLANT INCLUDING A BODY OF NON-RESORBABLE BIOACTIVE MATERIAL

THIS INVENTION relates to an implant. It relates also to a method of making an implant.

According to a first aspect of the invention, there is provided an implant, which includes a body of non-resorbable bioactive material, with zones of resorbable bioactive material located in the body of non-resorbable material, and with the sizes of a major proportion of the zones of resorbable material being from 10 to 500 microns.

By 'size' is meant the effective cross-sectional dimension of a zone of resorbable material. When the zones are spherical, their size is thus their diameter; however, when the zones are non-circular, their size is the same as the mesh size through which such zones of resorbable material will pass.

By 'a major proportion' in respect of the zones of resorbable material that are from 10 to 500 microns, is meant at least 50% of the zones. Preferably, however, at least 80% of the zones of resorbable material are from 10 to 500 microns.

In particular, the non-resorbable bioactive material may be hydroxyapatite, while the resorbable material may be tricalcium phosphate.

The hydroxyapatite of the body is in crystalline form, and is thus substantially non-resorbable in use. The tricalcium phosphate is also in crystalline form, and may be in either the $\alpha$ or the $\beta$ form, both of which are resorbable in use. However, the $\beta$ form is preferred.

Substantially all of the zones of tricalcium phosphate may be of the same size. The zones of the tricalcium phosphate may be randomly dispersed throughout the hydroxyapatite body. Some of the zones may thus be located at the surface of the body. The sizes of the zones may, in particular, be from 10 to 300 microns.

The proportion of hydroxyapatite to tricalcium phosphate in the implant may be from 4:1 to 2:3, on a mass basis, preferably about 2:1.

Macropores or macroporous spaces may be provided in the body. The macropores may be substantially spherical, and at least some of the macropores may be interconnected. In particular, the macropores that are interconnected may be of spherical, intercoalesced form, ie adjacent macropores may be coalesced together and thus not interconnected by elongate passageways.

The macropores may be from 100 to 2000 microns in size, ie may have diameters of 100 to 2000 microns, preferably 400 to 800 microns.

All, or at least a majority, of the macropores may be of substantially the same size. The macropores may occupy from 20% to 80% of the total volume of the body. For example, the macropores may occupy about 60% of the total volume of the body.

The macropores may be randomly interspersed throughout the body. Thus, the body may have a network of interconnected coalesced rounded inner macroporous spaces.

The body may also, if desired, be provided with surface concavities. The surface concavities may be rounded. The surface concavities may have diameters of from 100 to 2000 microns, preferably 200 to 400 microns, and depths of 100 to 1000 microns, preferably 200 to 500 microns, typically 200 to 400 microns.

The surface concavities may be hemispherical. The surface concavities may be interconnected with the macropores by being coalesced therewith.

If desired, micropores may also be provided in the body. While some of the micropores may also be substantially spherical, the majority of the micropores will normally be of irregular shape. The micropores may also be randomly interspersed throughout the body.

The majority of the micropores may be open micropores, ie open or connected to the surface and not necessarily connected together. The micropores may all be of substantially the same size, and may be smaller than 50 microns, ie have diameters smaller than 50 microns, preferably smaller than 10 microns.

The micropores, when present, may occupy 60% or less of the total volume of the body, excluding the volume occupied by the macropores, ie the residual volume of the body after the volume of the macropores has been excluded. Typically, the micropores may occupy about 40% of the residual body volume.

The implant is suitable for implanting into a subject. It can thus be used either as a bone implant at a site where bone growth is required, or as an implant in a site where only soft tissue is in direct contact with the implant without any bone being present in the immediate vicinity of the implant ie a soft tissue implant.

The hydroxyapatite and tricalcium phosphate are sintered bioactive ceramic biomaterials, and the implant has both intrinsic osteoconductivity, ie permitting bone growth into its pores or porous spaces when it is in direct contact with viable bone, and intrinsic osteoinductivity, ie permitting bone growth into its pores independently of the presence of viable bone in contact with the implant.

According to a second aspect of the invention, there is provided a method of making an implant, which method includes mixing a non-resorbable bioactive material in powder form with a thermoplastic binder at elevated temperature, to produce a first powder/binder mixture;

comminuting the first powder/binder mixture to obtain a first granular mixture having granules or particles with sizes from 10 to 500 microns;

mixing a resorbable bioactive material in powder form with a thermoplastic binder at elevated temperature, to produce a second powder/binder mixture;

comminuting the second powder/binder mixture to obtain a second granular mixture having granules or particles with sizes from 10 to 500 microns;

combining the first and second granular mixtures to form a combined mixture;

optionally, mixing the combined mixture with fugitive phase particles which are heat decomposable, with the fugitive phase particles having sizes of 100 to 2000 microns;

pressing or compacting the resultant mixture into a green compact or body;

when the fugitive phase particles are present, heating the green compacts or bodies to above the decomposition temperature of the fugitive phase particles; and sintering the resultant green body, to obtain an implant.

As hereinbefore described, the non-resorbable bioactive material may, in particular, be hydroxyapatite, while the resorbable material may be tricalcium phosphate.

Any suitable thermoplastic binder, such as a commercial polymeric binder used for extrusion or injection moulding of ceramic materials, may be used, provided it allows ambient temperature compaction of the granules to a strength adequate for further processing. The same thermoplastic binder may be used for the first and second powder/binder mixtures.

The temperature at which the mixing of the hydroxyapatite powder and the tricalcium phosphate powder with the thermoplastic binder to produce the first and second powder/binder mixtures takes place, depends on the thermoplastic binder used, but is typically about 120° C. The comminution of the first and second powder/binder mixtures may be effected by crushing the mixtures, and sieving them to the required granule or particle size.

In forming the combined mixture, the first and second mixtures are used in a desired mass ratio, depending on the desired relative portions of hydroxyapatite and tricalcium homogenizing the combined mixture in a ball mill without milling media, for an extended period of time, eg for a period of several hours.

The fugitive phase particles, when present, may be stearic acid particles, which may be substantially spherical. The stearic acid particles will be selected such that they provide macropores or macroporous spaces of a desired size in the implant. Thus, typically, stearic acid particles having a size range of 500 to 1000 microns are used.

The combined mixture is admixed with the fugitive phase particles in a desired mass ratio in order to provide a resultant implant having a desired macropore volume. Thus, if a desired macropore volume of approximately 60% of the total implant volume is desired, then the mass proportion of the combined mixture to fugitive phase particles will be about 1,27:1 by mass.

To form the green compact or body, the mixture may be pressed or compacted at a pressure of about 20 MPa and machined, if necessary.

The temperature to which the green compacts or bodies are heated is dependent on the fugitive phase used. However, when stearic acid particles are used as the fugitive phase, the green compacts are typically heated to about 500° C., to allow melting and decomposition of the stearic acid, thereby forming in the green compacts or bodies, interconnected macropores produced by the decomposition of the stearic acid particles. The sintering is thus effected at elevated temperature, ie at a temperature above 500° C. The sintering temperature and time is set or limited by the level of micropores required in the resultant implant. For example, to obtain a microporosity level or volume of 40% may be effected at about 1100° C. for one hour.

The invention will now be described in more detail, with reference to the accompanying drawing which show a cross-sectional view of an implant according to the first aspect of the invention.

In the drawing, reference numeral 10 generally indicates an implant according to the invention. The implant is shown as being circular in cross-section. This is for ease of illustration; in practice the implant shape and size will be dictated by its desired end use.

The implant 10 includes a body 12 of hydroxyapatite. Zones 14 of β-tricalcium phosphate are randomly dispersed throughout the body 12. The zones 14 are of approximately the same size, and have a size of about 300 microns.

The mass ration of hydroxyapatite to β-tricalcium phosphate in the implant 10 is approximately 2:1.

The implant 10 also includes a plurality of randomly interspersed spherical macropores, each generally indicated by reference numeral 16. Some adjacent macropores 16 are coalesced together so that the adjacent macropores 16 are connected together by means of a connecting line 18 rather than by means of elongate tunnels or passageways. The macropores 16 are all of approximately the same size, and they have diameters in the range of 400 to 800 microns. The macropores 16 occupy about 60% of the total volume of the implant 10.

The implant is also provided with randomly dispersed micropores 20 having a size smaller than 10 microns. While the micropores are shown as being spherical, in practice only some of the micropores will in fact be spherical; the majority thereof will be of irregular shape as a result of incomplete sintering. The individual micropores 20 are mostly open micropores, is open to the surface and not necessarily connected together. The micropores 20 are dispersed throughout the body 12 as well as throughout the zones 14. The micropores 20 occupy about 40% of the residual volume of the body 12, ie the volume of the body 12 remaining after the combined volume of all the macropores 16 have been deducted from the initial volume of the body 12.

The implant 10 is formed by compounding hydroxyapatite powder with a commercial thermoplastic polymeric binder at a temperature of about 120° C. to produce a first powder/polymer mixture. This mixture is crushed and sieved to a particle size smaller than 300 microns. In this fashion, a first granular mixture is obtained.

β-tricalcium phosphate powder is similarly compounded with the same thermoplastic polymeric binder at an elevated temperature of about 120° C., to produce a second powder/polymer mixture. This mixture is also crushed and sieved to a particle size smaller than 300 microns, to obtain a second granular mixture.

Any commercial thermoplastic polymeric binder suitable for extrusion or injection moulding of ceramic materials, may be used, provided it allows ambient temperature compaction of the granules of the mixtures to a strength adequate for further processing.

The first granular mixture is combined with the second granular mixture in a 2:1 ratio by mass, and homogenized by rolling thereof in a ball mill without milling media, for an extended period of several hours.

The resultant powder is mixed with substantially spherical particles of stearic acid which have been sieved to a size range of 500 to 1000 microns, with the mass proportion of powder to fugitive phase particles being 1,27:1. The resultant mixture is pressed or compacted at a pressure of 20 MPa, and machined if necessary. In this fashion, green compacts are obtained.

The green compacts are heated to 500° C., to allow melting and decomposition of the stearic acid particles, resulting in unsintered green compacts having interconnected coalesced macropores therein achieved by decomposition of the stearic acid particles.

The temperature is then further increased to achieve sintering of the hydroxyapatite and β-tricalcium phosphate powders. Micropores form in the body. The desired degree of microporosity is controlled by limiting the maximum conditions for sintering. For example, to achieve a microporosity level of 40% of the residual volume of the body, ie after the volume occupied by the macropores has been deducted from the initial volume of the implant body, sintering conditions are restricted to below 1100° C. for one hour.

The resultant implant has a final macroporous volume of approximately 60%, based on the total volume of the implant. The implant is suitable for use as a bone implant or as a soft tissue implant. When used as a bone implant, it has both osteoconductive and osteoinductive properties.

When used as either a bone implant or a soft tissue implant, the hydroxyapatite body 12 is essentially non-resorbable since it is in crystalline form. However, the β-tricalcium phosphate zones 14 are resorbable. Thus, the implant 10 has high bioactivity with partial controllable resorbability. Over time, all these zones 14 will resorb, leaving a skeleton or scaffold of hydroxyapatite, where bone growth can take place.

It is believed that, with the zones 14 which are larger than 10 microns, faster resorption of the tricalcium phosphate in these areas will take place than would be obtained with a finer distribution of tricalcium phosphate, eg single tricalcium phosphate particles in a mixture of such particles and hydroxyapatite particles. Penetration of hard or soft tissue then takes place into the ceramic structure at the locations where resorption of the tricalcium phosphate has occurred. This occurs while the basic ceramic hydroxyapatite scaffold is preserved.

What is claimed is:

1. An implant, which includes a body of hydroxyapatite, with zones of tricalcium phosphate randomly dispersed throughout the body of hydroxyapatite, and the sizes of a major proportion of the zones of tricalcium phosphate being from 10 to 500 microns, and with randomly interspersed macropores provided in the body.

2. An implant according to claim 1, wherein substantially all of the zones of tricalcium phosphate are of the same size.

3. An implant according to claim 1, wherein the size of the zones is from 10 to 300 microns.

4. An implant according to claim 1, wherein the proportion of hydroxyapatite to tricalcium phosphate in the implant is from 4:1 to 2:3, on a mass basis.

5. An implant according to claim 1, wherein the macropores are substantially spherical, with at least some of the macropores being interconnected by being coalesced together.

6. An implant according to claim 5, wherein the macropores are from 100 to 2000 microns in size.

7. An implant according to claim 5, wherein at least a majority of the macropores are of substantially the same size, and wherein the macropores occupy from 20% to 80% of the total volume of the body.

8. An implant according to claim 5, wherein the body is provided with source concavities.

9. An implant according to claim 8, wherein the surface concavities are rounded, having diameters of from 100 to 2000 microns.

10. An implant according to claim 8, wherein the surface concavities are hemispherical and are interconnected with the macropores by being coalesced therewith.

11. An implant according to claim 1, wherein the body has a network of interconnected coalesced rounded inner macroporous spaces.

12. An implant according to claim 1, which includes micropores, with the micropores being randomly interspersed throughout the body of hydroxyapatite as well as throughout the zones of tricalcium phosphate.

13. An implant according to claim 12, wherein the micropores are all of substantially the same size, and are smaller than 50 microns.

14. An implant according to claim 12, wherein the micropores occupy 60% or less of the total volume of the body, excluding the volume occupied by the macropores.

15. An implant, which includes a body of hydroxyapatite, with zones of tricalcium phosphate randomly dispersed throughout the body of hydroxyapatite and with the sizes of a major proportion of the zones of tricalcium phosphate being from 10 to 500 microns, and which includes micropores, with the micropores being randomly interspersed throughout the body of hydroxyapatite as well as throughout the zones of tricalcium phosphate.

16. An implant according to claim 15, wherein substantially all of the zones of tricalcium phosphate are of the same size, and are from 10 to 300 microns.

17. An implant according to claim 15, wherein the proportion of hydroxyapatite to tricalcium phosphate in the implant is from 4:1 to 2:3, on a mass basis.

18. An implant according to claim 15, wherein the micropores are all of substantially the same size, and are smaller than 50 microns.

19. A method of making an implant, which method includes mixing a non-resorbable bioactive material in powder form with a thermoplastic binder at elevated temperature, to produce a first powder/binder mixture;

comminuting the first powder/binder mixture to obtain a first granular mixture having granules or particles with sizes from 10 to 500 microns;

mixing a resorbable bioactive material in powder form with a thermoplastic binder at elevated temperature, to produce a second powder/binder mixture;

comminuting the second powder/binder mixture to obtain a second granular mixture having granules or particles with sizes from 10 to 500 microns;

combining the first and second granular mixtures to form a combined mixture;

optionally, mixing the combined mixture with fugitive phase particles which are heat decomposable, with the fugitive phase particles having sizes of 100 to 2000 microns;

pressing or compacting the resultant mixture into a green compact or body;

when the fugitive phase particles are present, heating the green compacts or bodies to above the decomposition temperature of the fugitive phase particles; and sintering the resultant green body, to obtain an implant.

20. A method according to claim 19, wherein the non-resorbable bioactive material is hydroxyapatite, while the resorbable material is tricalcium phosphate.

21. A method according to claim 20, wherein the temperature at which the mixing of the hydroxyapatite powder and the tricalcium phosphate powder with the thermoplastic binder to produce the first and second powder/binder mixtures takes place, is about 120° C., and wherein the comminution of the first and second powder/binder mixtures is effected by crushing the mixtures, and sieving them to the required granule or particle size.

22. A method according to claim 20, wherein the fugitive phase particles are present and are spherical stearic acid particles having a size range of 500 to 1000 microns.

23. A method according to claim 22, wherein the mass proportion of the combined mixture to fugitive phase particles is about 1,27:1 by mass, to obtain an implant having a macropore volume of approximately 60% of the total implant volume.

24. A method according to claim 22, wherein the green compacts are heated to about 500° C., to allow melting and decomposition of the stearic acid, thereby forming, in the green compacts or bodies, interconnected macropores produced by the decomposition of the stearic acid particles.

25. A method according to claim 24, wherein, to obtain a microporosity level or volume of 40% of the residual solid component of the implant, the sintering is effected at about 1100° C. for one hour.

* * * * *

UNITED STATES PATENT AND TRADEMARK OFFICE
CERTIFICATE OF CORRECTION

PATENT NO. : 6,858,041 B2
DATED : February 22, 2004
INVENTOR(S) : Paul Wilhelm Richter et al.

It is certified that error appears in the above-identified patent and that said Letters Patent is hereby corrected as shown below:

Column 5,
Line 39, change "source" to -- surface --.

Signed and Sealed this

Twenty-fourth Day of May, 2005

JON W. DUDAS
*Director of the United States Patent and Trademark Office*